(12) United States Patent
Curry

(10) Patent No.: US 8,251,952 B2
(45) Date of Patent: Aug. 28, 2012

(54) AIRLESS INTRAVENOUS BAG

(76) Inventor: Jeremy Scott Curry, Yuma, AZ (US)

( * ) Notice: Subject to any disclaimer, the term of this patent is extended or adjusted under 35 U.S.C. 154(b) by 601 days.

(21) Appl. No.: 12/351,636

(22) Filed: Jan. 9, 2009

(65) Prior Publication Data

US 2009/0192459 A1     Jul. 30, 2009

Related U.S. Application Data

(60) Provisional application No. 61/062,751, filed on Jan. 30, 2008.

(51) Int. Cl.
*A61M 1/00* (2006.01)
*A61M 5/00* (2006.01)
*A61M 5/14* (2006.01)
*A61B 19/00* (2006.01)

(52) U.S. Cl. ........ 604/122; 604/254; 604/260; 604/403; 604/404; 604/407

(58) Field of Classification Search ............... 604/410, 604/403, 404, 405, 406, 407, 122, 246, 254, 604/260; 128/214
See application file for complete search history.

(56) References Cited

U.S. PATENT DOCUMENTS

| | | | |
|---|---|---|---|
| 2,693,801 A | 11/1954 | Foreman | |
| 2,853,069 A | 9/1958 | Beacham et al. | |
| 3,304,977 A | 2/1967 | Hammons | |
| 3,648,697 A * | 3/1972 | Gardner | 604/408 |
| 4,055,176 A * | 10/1977 | Lundquist | 604/127 |
| 4,177,808 A | 12/1979 | Malbec | |
| 4,187,847 A | 2/1980 | Loeser | |
| 4,195,633 A * | 4/1980 | Nehring et al. | 604/318 |
| 4,267,834 A * | 5/1981 | Barger et al. | 604/250 |
| 4,396,383 A | 8/1983 | Hart | |
| 4,553,970 A * | 11/1985 | Lewis, Jr. | 604/408 |
| 4,639,251 A | 1/1987 | Kirkland | |
| 4,923,438 A * | 5/1990 | Vasconcellos et al. | 604/6.15 |
| 4,952,210 A * | 8/1990 | Alchas | 604/251 |
| 4,994,050 A * | 2/1991 | Weilbacher et al. | 604/320 |
| 5,257,985 A * | 11/1993 | Puhl | 604/410 |
| 5,286,262 A * | 2/1994 | Herweck et al. | 604/321 |
| 5,352,213 A | 10/1994 | Woodard | |
| 5,382,244 A * | 1/1995 | Telang | 604/319 |
| 5,397,299 A * | 3/1995 | Karwoski et al. | 604/6.1 |
| 5,560,403 A | 10/1996 | Balteau et al. | |
| 5,575,779 A * | 11/1996 | Barry | 604/246 |
| 5,728,077 A * | 3/1998 | Williams et al. | 604/246 |
| 5,853,388 A | 12/1998 | Semel | |
| 6,231,559 B1 | 5/2001 | Loretti | |
| 6,261,267 B1 * | 7/2001 | Chen | 604/247 |
| 6,364,864 B1 | 4/2002 | Mohiuddin et al. | |
| 6,432,083 B1 * | 8/2002 | Raschbaum | 604/118 |

(Continued)

OTHER PUBLICATIONS

Search Report dated Sep. 23, 2009, issued in Application No. PCT/US2009/052040.

(Continued)

*Primary Examiner* — Tatyana Zalukaeva
*Assistant Examiner* — Xin Xie
(74) *Attorney, Agent, or Firm* — Bryan Cave LLP

(57) ABSTRACT

The present disclosure provides for an airless intravenous (IV) bag which contains a specialized device, referred to herein as the airless intravasculature infusion device (AIVID). The AIVID allows one to view the amount of fluid in the IV bag but substantially decreases or completely prohibits the risk of an inadvertent air infusion into a patient.

20 Claims, 6 Drawing Sheets

U.S. PATENT DOCUMENTS

| | | | |
|---|---|---|---|
| 6,663,829 B1 * | 12/2003 | Kjellstrand | 422/1 |
| 6,800,072 B2 * | 10/2004 | Patzer | 604/260 |
| 6,877,877 B2 | 4/2005 | Rodriguez et al. | |
| 7,879,014 B2 * | 2/2011 | Mottola | 604/254 |
| 2002/0038572 A1 * | 4/2002 | Drinkwater | 73/323 |
| 2002/0115965 A1 * | 8/2002 | Jang et al. | 604/254 |
| 2005/0171491 A1 * | 8/2005 | Minh Miner et al. | 604/257 |
| 2005/0177128 A1 | 8/2005 | Nagao et al. | |
| 2006/0129111 A1 * | 6/2006 | Mottola | 604/254 |

OTHER PUBLICATIONS

Written Opinion dated Sep. 23, 2009, issued in Application No. PCT/US2009/052040.

\* cited by examiner

AIRLESS INTRAVENOUS BAG

CLAIM TO DOMESTIC PRIORITY

This application claims priority to and the benefit of the filing date of U.S. Provisional Patent Application No. 61/062,751, filed Jan. 30, 2008, entitled "Airless Intravenous Bag," which application is hereby incorporated in its entirety.

FIELD OF THE INVENTION

The present invention relates to the field of intravenous bag systems, and more particularly, to an airless intravenous bag system that eliminates the need for priming the intravenous line when exchanging intravenous bags.

BACKGROUND

In conventional intravenous bag systems when the bags are totally depleted (i.e. "run dry"), the previously placed air then is allowed to leave the bag. This usually then fills the drip chamber and the plastic tubing of the intravenous line. This can be problematic in many settings.

Once the tubing has air inside of it, a new bag must be hung, the tubing transferred to it, and the line must be re-primed. Re-priming involves placing a syringe and needle into a port on the intravenous tubing and withdrawing the air from the tubing. This takes time that can be problematic when the patient needs intravenous medications or acute fluid administration for a sudden change in their vital signs (i.e. blood pressure, heart rate, etc.). In fact, these intravenous bags usually are not noticed "running dry" during emergencies because everyone's attention is usually focused on other things. During true emergent traumas, a patient may be getting intravenous solution more rapidly then with the standard gravity drip. Often times the intravenous bags are placed in pressurized bags or machines that literally squeeze the bag forcing the solution into the patient via the intravenous tubing. Unfortunately, when all the fluid is pressurized out of the bag, the entrapped air is next forced through the intravenous tubing, potentially into the patient.

Air in the intravenous tubing is potentially disastrous because enough air may cause a "vapor-lock" phenomena whereby the right ventricle of the heart fills with air. Normal contractions are ineffective to push blood through the pulmonary vasculature where it is oxygenated and delivered to the left ventricle to be pushed out and circulated into the body. In other words, vapor-lock is a sudden cardiovascular collapse where no more blood can be circulated. An adult would need a high amount of air but a pediatric patient with a smaller heart would require much less air to cause this fatal scenario. Another potential problem is that air may not collect in the right ventricle, but may get pushed into the pulmonary vasculature. The name for this potentially lethal event is called pulmonary embolism. Air may get stuck in the pulmonary capillaries. This causes an increased resistance to the normal forward flow to the left atrium of blood. This increased resistance may cause the right side of the heart to fail, also since blood is not being circulated, the oxygen content falls, and since it is not getting to the left side of the heart, the output from the heart into the body drops to critical levels.

The above two scenarios are certainly possible but require large amounts of air. The most likely scenario for air entering into the vasculature and causing a devastating complication is via a probe patent or even an open Foramen Ovale. Bile Foramen Ovale is a unique fetal adaptation the human heart has while the fetus in the uterus. Blood is shunted away from the lungs (since the fetus is not breathing) and into the main vasculature. One way this blood is shunted past the lungs in through a hole in the septum between the right and left atrium of the heart. This hole is called the Foramen Ovale. Normally this hole closes right after birth as the human heart now directs blood into the lungs than past them.

Unfortunately, in up to 15% of adults and a much higher corresponding level of neonates and children, this percentage is even higher. Probe patent means that a probe can be pushed through the Foramen Ovale which is only partially closed, or in other situations, it might be completely open. If a small air bubble makes it to the right atrium, the normal mechanism of passing into the right ventricle and then getting lodged into the palmary vasculature is bypassed. Instead, this air bubble may pass through the Foramen Ovale into the left atrium (bypassing the lungs), entering into the left ventricle, and then squeezed out into the body. If this air bubble goes to the brain, a devastating stroke may ensue. Central lines, which are long catheters intravenously placed into large veins and threaded close to the heart are more likely to cause this situation, however, even a small peripheral intravenous line can still elicit this situation especially in the setting of a small pediatric patient.

The above reasons are why medical practitioners are so adamant on not allowing any air to pass into the patient. Unfortunately, with the current intravenous bags that are in use today, this is a constant threat.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings.

DETAILED DESCRIPTION OF THE FIGURES

The present disclosure provides for an airless intravenous (IV) bag which contains a specialized device, referred to herein as the airless intravasculature infusion device (AIVID). The AIVID allows one to view the amount of fluid in the IV bag and substantially decrease or completely prohibit the risk of an inadvertent air infusion.

In the following description, numerous specific details are set forth in order to provide a thorough understanding of the present invention. It will be obvious, however, to one skilled in the art that the present invention may be practiced without these specific details. In other instances, well-known aspects of intravenous bag systems have not been described in particular detail in order to avoid unnecessarily obscuring the present invention.

Figure 1:
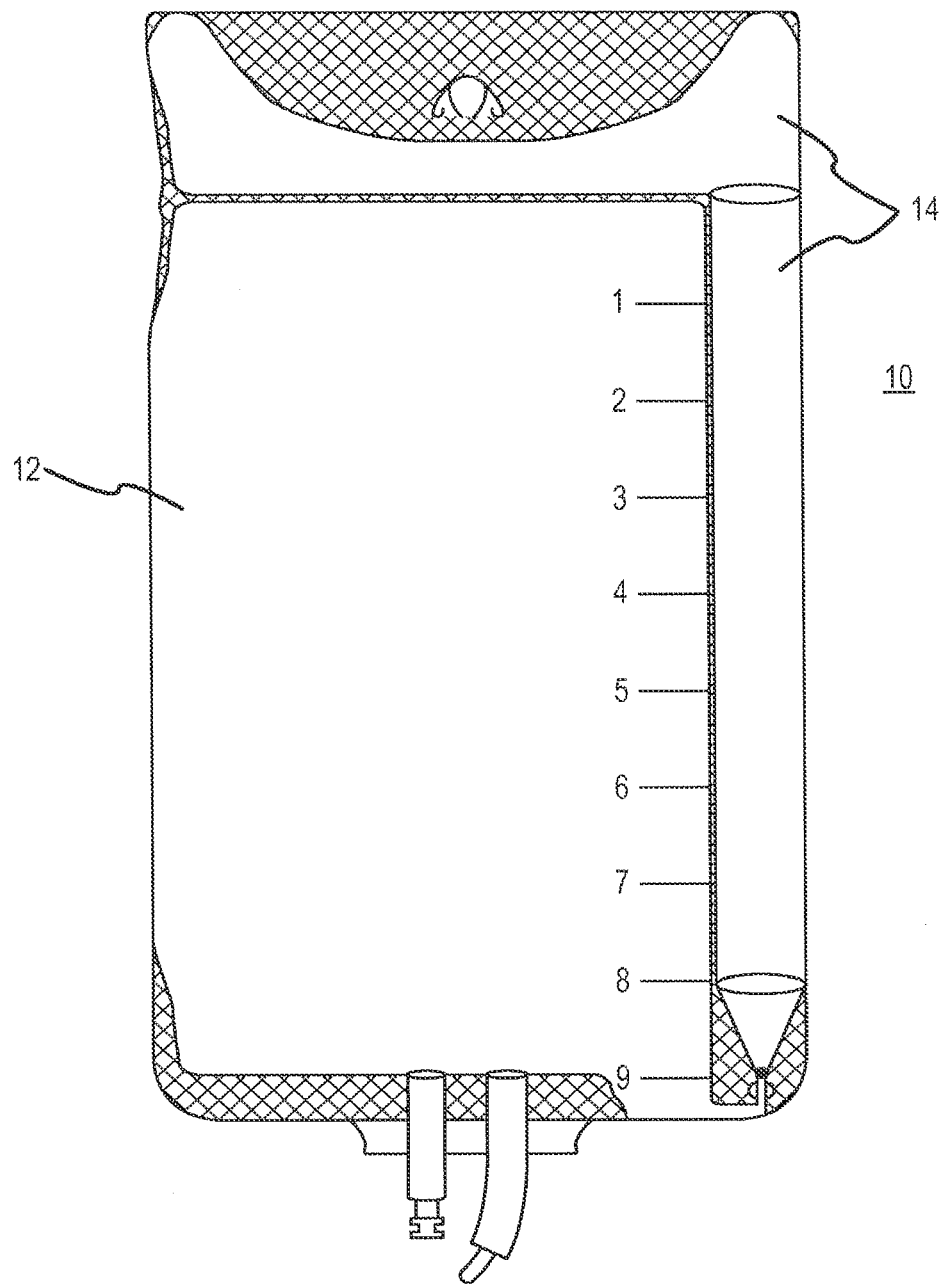
FIG. 1 is a front view of an airless intravenous bag according to one embodiment of the disclosure.

As shown in FIG. 1, the disclosed airless intravenous bag 10 comprises a standard pliable plastic IV bag that is divided into two asymmetrical compartments along its vertical axis the larger of the two compartments, referred to herein as the IV solution compartment 12 holds the IV solution to be infused into the patient devoid of any air. IV solution compartment 12 is comprised of a pliable plastic bag. The second, smaller compartment is air chamber 14.

Figure 2:
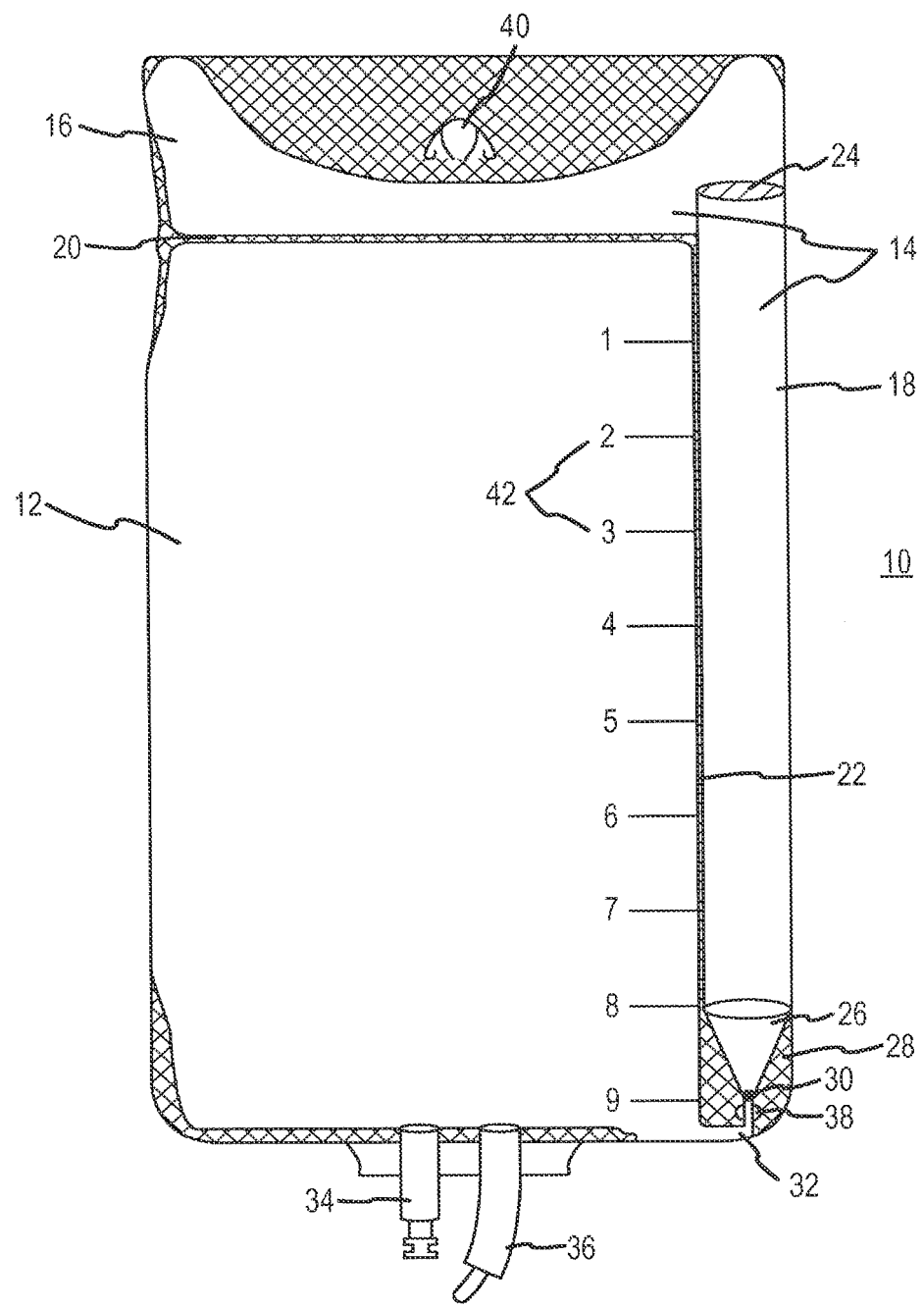
FIG. 2 is a further illustration of the airless intravenous bag according to one embodiment of the disclosure.

As shown in further detail in FIG. 2, air chamber 14 is comprised of two parts, air reservoir 16 and air column 18. The air reservoir 16 is separated from the IV solution compartment 12 by horizontal seam 20. Air reservoir 16 is also comprised of the same pliable plastic material as IV solution compartment 12. Air column 18 is comprised of a hard plastic column separated from IV solution compartment 12 by vertical seam 22. Air column 18 also comprises a mesh network 24 at the top of air column 18, and between air reservoir 16 and air column 18. Air column 18 terminates into funnel aperture 26.

Surrounding funnel aperture 26 is airless intravasculature infusion device (AIVID) 28. AIVID 28 is constructed of soft pliable plastic and include hard plastic half beads 38 embedded within the soft pliable plastic matrix of AIVID 28. Shown in FIG. 2 at the base of funnel aperture 26 is buoyant bead 30. Extending down vertically from funnel aperture 26 and into IV solution compartment 12 is solution channel 32. IV solution compartment 12 then terminates at its base with an injection port 34 and a docking port 36 for the IV drip chamber.

IV bag 10 also comprises a pre-cut tab 40 for hanging the IV bag 10, as needed, and printed measurement markings 42 on the outside of IV bag 10.

Figure 3:
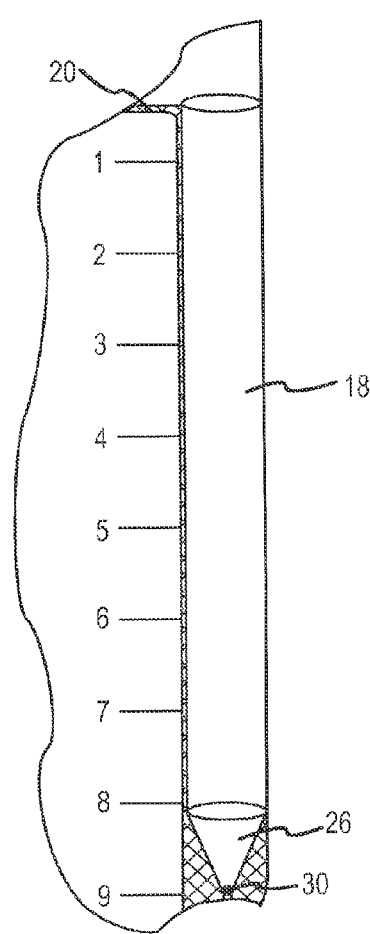
FIGS. 3 and 4 are further illustrations of the second chamber of the airless intravenous bag according to one embodiment of the disclosure.
Figure 4:
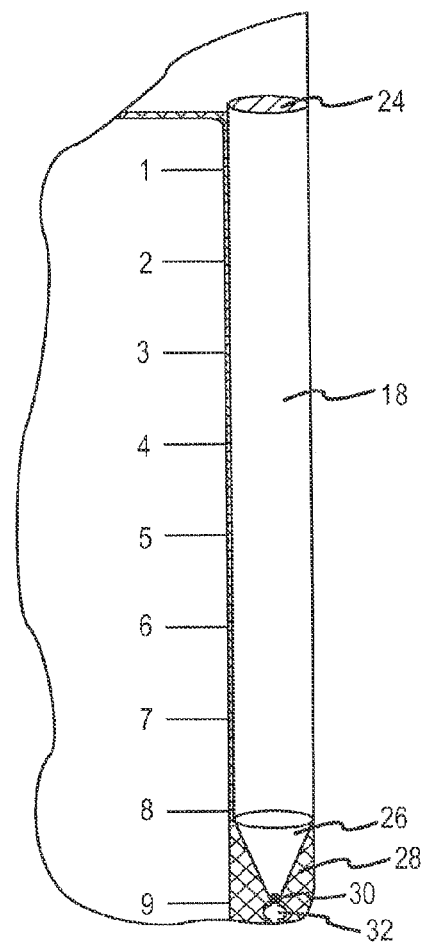

Turing now to FIG. 3 and FIG. 4, air column 18 and its features are illustrated in further detail. The IV solution compartment 12 is connected to AIVID 28 at the base of IV bag 12. AIVID 28 is a small less pliable plastic component that has a small channel (solution channel 32) through it center that connects it to air column 18 (part of air chamber 14). Air column 18 also contains the top of the AIVID 28 which forming a funnel that decreases in size from top to bottom, referred to herein as funnel aperture 26. Stretching upwards from funnel aperture 26 is a long clear harder plastic tube, as described above, air column 18. Air column 18 is designed so that it cannot be easily compressed.

As shown specifically in FIG. 4, the top of air column 18 has a thin mesh, namely mesh network 24, over the top of air column 18, but still opens into a small compartment, air reservoir 16 where air can be stored. As noted above, air reservoir 16 is comprised of the same pliable material as the IV solution compartment 12.

Figure 9:
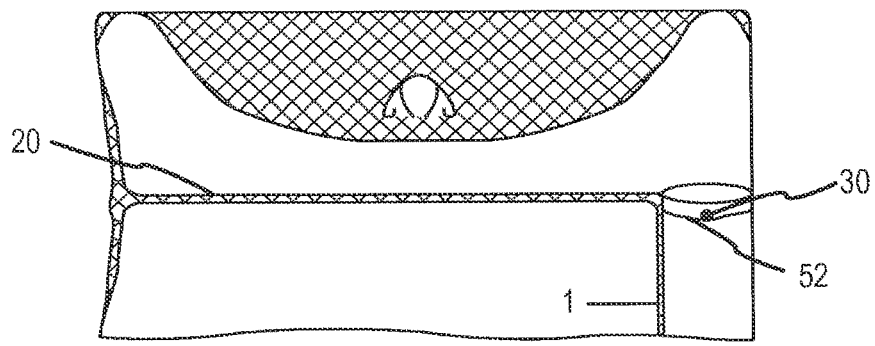
FIG. 9 is a front view of the airless intravenous bag shown filled with I.V. solution.
Figure 10:
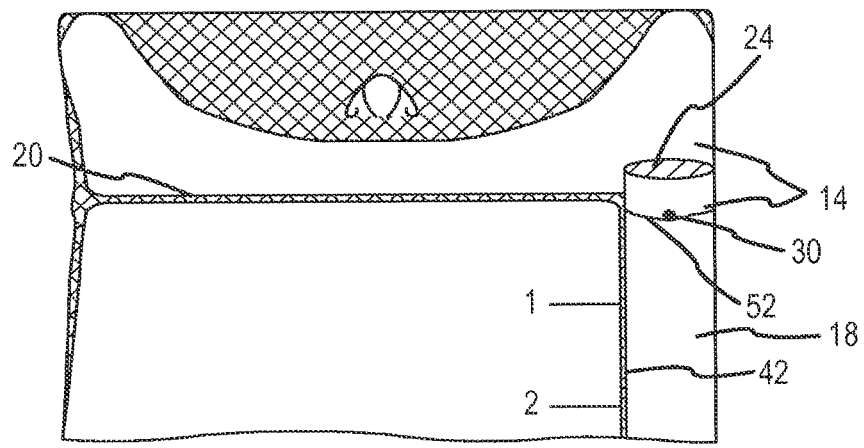
FIG. 10 is a further illustration of the airless intravenous bag shown filled with I.V. solution.

As shown in FIGS. 9 and 10, the primary purpose of the air reservoir 16 is to allow one to visualize the fluid level 52, including the remaining fluid in the IV solution compartment 12 without the risk of inadvertent air administration. As shown in FIGS. 9 and 10, this is accomplished with a small blue or red colored buoyant bead 30 that floats on the surface of the IV solution in solution channel 32.

Figure 6:
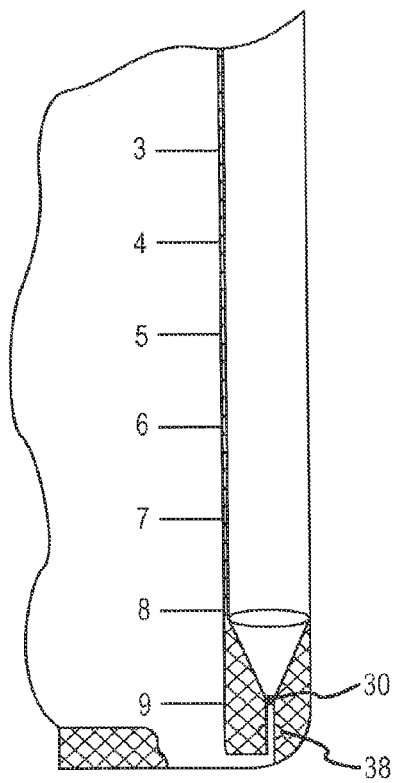
FIG. 6 is a front view of the airless intravenous bag in the closed position.
Figure 8:
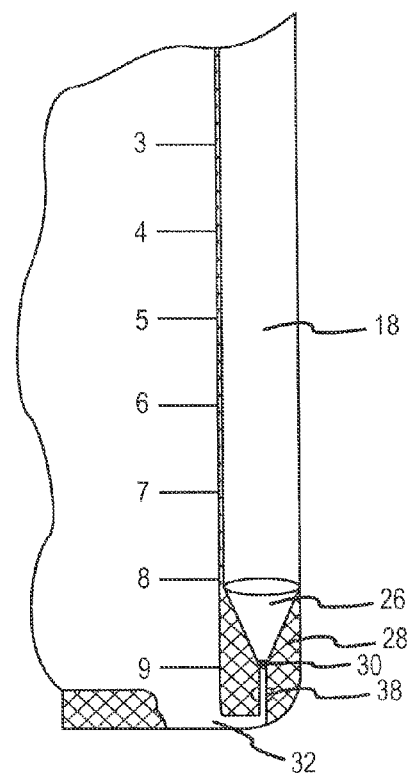
FIG. 8 is a further illustration of the airless intravenous bag in the closed position.

Turning now to FIGS. 6 and 8, when the buoyant bead is just below the funnel aperture 26 in AIVID 28, this is considered the closed position. FIGS. 6 and 8 specifically illustrate the details of the "closed position" of IV bag 10. The "closed position" is required for shipping purposes. Specifically, when IV bag 10 with buoyant bead 30 is in the closed position, a barrier is formed effectively blocking the solution channel 32 so that IV solution and/or air cannot traverse to opposite sides (enter each other's compartments). This is facilitated by the tight fit of the buoyant bead 30 within the AIVID 28. The "closed position" may also be referred to as the "locked position."

Then when the IV bag 10 is hung and ready for use, the medical professional then pinches the AIVID 28, at half beads 38, between his fingers. The directed pressure of the fingers being squeezed on each half bead 38 in AIVID 28 is sufficient to squeeze the buoyant bead 30 from its "closed" or "locked" position. The buoyant bead 30 then rises upwards into funnel aperture 26, as described below with reference to FIGS. 5 and 7.

Figure 5:
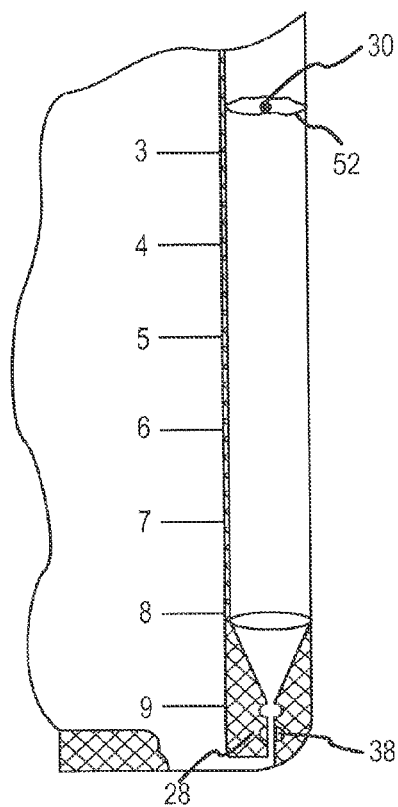
FIG. 5 is a front view of the airless intravenous bag in the open position.
Figure 7:
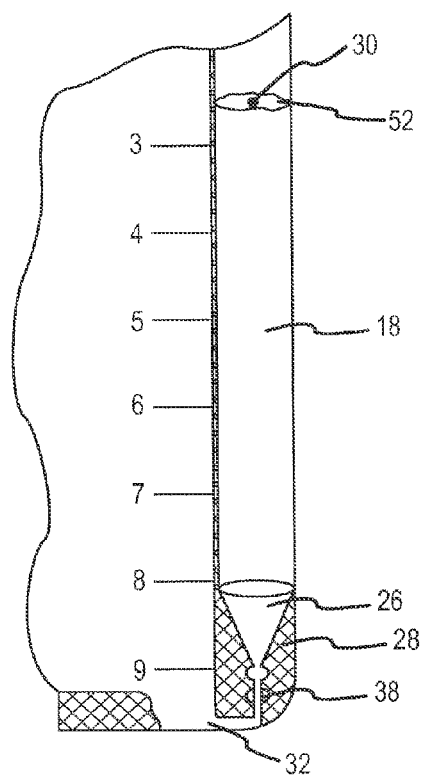
FIG. 7 is a further illustration of the airless intravenous bag in the open position.

As shown in FIGS. 5 and 7, the IV bag 10 is now in the "open position." Once the buoyant bead 30 has been dislodged from the solution channel 32, IV solution is allowed to rush upwards filling air column 18. Air column 18 will fill to a level (meniscus 52) corresponding to the level of the IV solution in IV solution compartment 12. As air column 18 fills with IV solution, the air in air column 18 is pushed into air reservoir 16 through mesh network 24. Mesh network 24 at the top of air column 18 serves to keep the buoyant bead 30 from inadvertently entering the air reservoir 16 and becoming trapped.

As noted above in reference to FIGS. 9 and 10, measurement numbers 42 and corresponding lines are printed on the outside of IV bag 10 so that the medical professional may observe the amount of IV solution being used. The medical professional can then easily view the amount of IV solution left by visualizing the buoyant bead 30 on the meniscus 52 formed within air column 18 and then comparing that to corresponding measurement number 42 printed on the outside of IV bag 10.

As the IV solution is dispensed, the IV solution compartment 12 empties. As the IV solution compartment 12 empties, the fluid level (indicated by meniscus 52) within the air column 18 also begins to drop. Air from air reservoir 16 then replaces the vacant space left by the dropping meniscus 52. A particular unique and novel feature of IV bag 10 is that when the IV solution compartment 12 reaches a very low residual volume, the meniscus 52 begins to drop into the funnel aperture 26 of the AIVID 28. As this happens, buoyant bead 30 floating on the surface of meniscus 52 is slowly aligned to the center by the walls of funnel aperture 26. As the very last amount of IV solution is draining from the IV bag 10, and consequently also from air column 18 through solution channel 32, buoyant bead 30 is guided down atop the opening to solution channel 32. This effectively blocks any air from crossing back through solution channel 32 into IV solution compartment 12. In preventing air from crossing back into IV solution compartment 12 this consequently also prevents air from entering into the IV tubing itself.

Thus, when the IV bag 10 is completely emptied, or "runs dry," the IV solution compartment 12 completely collapses forming a small vacuum force that is transmitted through the solution channel 32 of AIVID 28. This in turn then holds buoyant bead 30 tightly locked in the opening of solution channel 32 at the bottom of funnel aperture 26. This in turn effectively blocks any air from passing into intravenous solution compartment 12.

When IV bag 10 runs dry, it simply stops dripping. The IV solution from compartment 12 and IV tubing in docketing station 36 stop flowing. The result is that no air enters the line and another bag can be hung without the need for priming the line.

Therefore, this new novel airless intravenous bag system allows a medical professional or other user to accurately measure the amount of IV fluid given, while reducing the risk of an inadvertent air infusion. Ultimately then, the presently disclosed airless intravenous bag system reduces or eliminates the potentially life threatening or disabling consequences of air infusion into a patient via the IV line.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An airless intravenous bag system, comprising:
    an intravenous bag including an intravenous solution compartment and an air chamber separated by one or more air tight seams, the air chamber further including an air column and an air reservoir separated by a mesh network;
    a funnel aperture, wherein the funnel aperture is positioned inside a bottom of the air column and is surrounded by an airless intravasculature infusion device that is positioned inside the air column; said airless intravasculature infusion device containing two half beads positioned at a base of the funnel aperture, the two half beads capable of being squeezed together;
    a buoyant bead inside the air column, wherein the buoyant bead is positioned in a locked position at the base of the funnel aperture when the intravenous bag is transported with intravenous solution in the intravenous solution compartment; and
    a solution channel of constant cross section extending from a position below the buoyant bead when in the locked position and into a bottom of the IV solution compartment, wherein the two half beads are embedded in the walls of said solution channel of constant cross section.

2. The airless intravenous bag system of claim 1, wherein when the buoyant bead is positioned at the base of the funnel aperture, a barrier is formed blocking the solution channel so that intravenous solution cannot traverse into the air chamber.

3. The airless intravenous bag system of claim 1, wherein when the buoyant bead is positioned at the base of the funnel aperture, a barrier is formed blocking the solution channel so that air cannot traverse into the intravenous solution compartment.

4. The airless intravenous bag system of claim 1, wherein a user pinches the two half beads together releasing the buoyant bead from the base of the funnel aperture allowing intravenous solution to flow through the solution channel into the air column.

5. The airless intravenous bag system of claim 4, wherein the intravenous solution flows through the solution channel filling the air column to the same level as the intravenous solution in the intravenous solution compartment.

6. The airless intravenous bag system of claim 4, wherein the intravenous solution forms a meniscus in the air column.

7. The airless intravenous bag system of claim 6, wherein the buoyant bead rises from the base of the funnel aperture to the level of the meniscus in the air column.

8. The airless intravenous bag system of claim 7, wherein the level of the buoyant bead corresponds to the level of the intravenous solution in the intravenous solution compartment.

9. The airless intravenous bag system of claim 1, further including measurement numbers on the outside of the airless intravenous bag useful for determining the amount of intravenous solution in the intravenous solution compartment.

10. The airless intravenous bag system of claim 7, wherein the level of the buoyant bead in the air column descends as the intravenous solution in the intravenous solution compartment empties, wherein the level of the buoyant bead is substantially the same level as the intravenous solution in the intravenous solution compartment providing an indicator as to the amount of remaining intravenous solution in the intravenous solution compartment.

11. The airless intravenous bag system of claim 4, wherein air flows through the mesh network into the air reservoir as the intravenous solution flows into the air column.

12. The airless intravenous bag system of claim 1, further including an injection port at the base of the intravenous solution compartment.

13. The airless intravenous bag system of claim 1, further including a docking port at the base of the intravenous solution compartment.

14. The airless intravenous bag system of claim 1, further including a pre-cut tab for hanging the airless intravenous bag.

15. The airless intravenous bag system of claim 1, wherein the level of intravenous solution in the air column empties through the solution channel so that the level of the intravenous solution in the air column is substantially the same as the level of the intravenous solution in the intravenous solution compartment.

16. The airless intravenous bag system of claim 15, wherein air from the air reservoir reenters the air column as the intravenous solution in the air column empties through the solution channel.

17. The airless intravenous bag system of claim 10, wherein the buoyant bead is aligned in the center of the funnel aperture when the intravenous solution reaches a very low level.

18. The airless intravenous bag system of claim 17, wherein the buoyant bead returns to the base of the funnel aperture atop the opening of the solution channel when the intravenous solution in the intravenous solution compartment is completely emptied, forming a vacuum and preventing air from passing into the intravenous solution compartment and into an intravenous line that is connected to the intravenous solution compartment via a docking port.

19. An airless intravenous bag system, comprising:
    an intravenous bag including an intravenous solution compartment and an air chamber separated by one or more air tight seams, the air chamber further including an air column and an air reservoir separated by a mesh network;
    a funnel aperture, wherein the funnel aperture is positioned inside a bottom of the air column and is surrounded by an airless intravasculature infusion device that is positioned inside the air column; said airless intravasculature infusion device containing two half beads positioned at a base of the funnel aperture;
    a buoyant bead inside the air column, wherein the buoyant bead is positioned in a locked position at the base of the funnel aperture when the intravenous bag is transported with intravenous solution in the intravenous solution compartment, and wherein the buoyant bead is positioned at the base of the funnel aperture when the intravenous solution compartment is empty; and
    a solution channel of constant cross section extending from a position below the buoyant bead when in the locked position and into a bottom of the IV solution compartment, wherein the two half beads are embedded in the walls of said solution channel of constant cross section.

20. The airless intravenous bag system of claim 19, wherein the buoyant bead at the base of the funnel aperture atop the opening of the solution channel forms a vacuum preventing air from passing into the intravenous solution compartment and into an intravenous line that is connected to the intravenous solution compartment.

* * * * *